United States Patent [19]

Shaffer et al.

[11] 4,181,631

[45] Jan. 1, 1980

[54] ALPHA-HYDROXYALKYL-4-TERTIARY-ALKYLCYCLOHEXANE PERFUME COMPOSITIONS

[75] Inventors: Gary W. Shaffer, Trumbull, Conn.; Kenneth L. Purzycki, Lake Parsippany, N.J.

[73] Assignee: Givaudan Corporation, Clifton, N.J.

[21] Appl. No.: 764,668

[22] Filed: Feb. 1, 1977

Related U.S. Application Data

[63] Continuation-in-part of Ser. No. 541,027, Feb. 12, 1975, abandoned.

[51] Int. Cl.$^2$ .............................................. C11B 9/00
[52] U.S. Cl. .............................. 252/522; 260/586 R; 260/586 C; 260/586 P; 252/174; 252/174.11; 424/69; 424/358; 424/364; 568/822
[58] Field of Search .................... 252/522; 260/617 R

[56] References Cited

U.S. PATENT DOCUMENTS

| | | | |
|---|---|---|---|
| 2,435,403 | 2/1948 | Morris et al. | 260/617 R |
| 3,514,489 | 5/1970 | Lemberg | 260/617 R |

FOREIGN PATENT DOCUMENTS

| | | |
|---|---|---|
| 1101409 | 1/1959 | Fed. Rep. of Germany . |
| 1106761 | 11/1961 | Fed. Rep. of Germany . |
| 1768633 | 6/1968 | Fed. Rep. of Germany . |
| 2656405 | 6/1977 | Fed. Rep. of Germany . |
| 1294931 | 4/1962 | France .................................. 260/617 R |

OTHER PUBLICATIONS

House et al., J. Org. Chem., vol. 33, (3), pp. 943–949, 1968.
Mori, Bull. Chem. Soc. Japan, vol. 34, pp. 1567–1569, 1961.
Stolow et al., J. Org. Chem., vol. 26, pp. 4726–4727, 1961.

*Primary Examiner*—Veronica O'Keefe
*Attorney, Agent, or Firm*—Robert F. Tavares; Thomas Cifelli, Jr.

[57] ABSTRACT

Novel α-hydroxyalkyl-4-t-alkylcyclohexanes possessing a sandalwood note, their utility as olfactory agents, and perfume compositions containing them.

26 Claims, No Drawings

ALPHA-HYDROXYALKYL-4-TERTIARY-ALKYL-CYCLOHEXANE PERFUME COMPOSITIONS

This application is a continuation-in-part of Ser. No. 541,027 filed Feb. 12, 1975 and now abandoned.

BACKGROUND OF THE INVENTION

1. Field of the Invention
Novel carbocyclic odorants.
2. The Prior Art

According to Guenther (E. Guenther, "The Essential Oils", Vol. V, page 173, D. Van Nostrand Co., Inc., New York (1952), East Indian Sandalwood Oil "has been perhaps one of the most precious perfumery materials from antiquity down to modern times, and its popularity has shown no signs of waning."

As with many other natural materials which contribute highly desirable nuances to perfume compositions, East Indian Sandalwood Oil is subject to the vagaries of natural products. Perfumers are necessarily restricted in the use of this valuable ingredient because of its high cost and limited supply.

The major constituents of sandalwood oil, α- and β-santalol, are known to be mainly responsible for its desired odor. There is, however, no commercially feasible process for the synthesis of these compounds. Accordingly, there is a continuing effort to provide synthetic materials which possess a sandalwood odor. Consequently, any substances possessing a sandalwood odor which are economical, and can be made readily available, will find immediate and appreciable commercial interest as a replacement or partial replacement for natural sandalwood oil in fragrance compositions.

SUMMARY OF THE INVENTION

In accordance with the present invention there is provided novel α-hydroxyalkyl-4-t-alkylcyclohexanes and perfume compositions containing same. The novel compounds of this invention can be represented by the general formula:

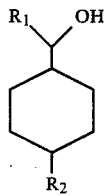

wherein $R_1$ represents an alkyl group of from one to three carbons and $R_2$ represents a tertiary alkyl group wherein the tertiary carbon is bonded to the cyclohexane ring. The compounds are further defined by requiring that the total number of carbons in $R_1+R_2$ not exceed ten. It should also be understood that $R_2$, the tertiary alkyl group, shall include both aliphatic t-alkyl groups and alicyclic t-alkyl groups.

It is the surprising and unexpected finding that the novel secondary alcohols of this invention possess the fine, precious, woody notes reminiscent of sandalwood oil. These compounds have simple monocyclic structures which are totally unrelated to the more complex structures of α-and β-santalol. It is also surprising that while the secondary alcohols of this invention all possess the sandalwood notes (differing from one another only in degree) the corresponding primary and tertiary alcohols are devoid of sandalwood notes. Similarly, the corresponding secondary alcohols wherein $R_2$ was not a tertiary alkyl group, lacked the fine sandalwood quality of the claimed compounds.

The compounds of this invention can be prepared in a variety of ways. The method which might be preferred in each case will normally be determined by the cost and availability of the required starting material. In general, the compounds can be prepared from appropriate t-alkylbenzenes or 4-t-alkylcyclohexanones by a variety of methods, some of which are indicated in Chart I.

CHART I

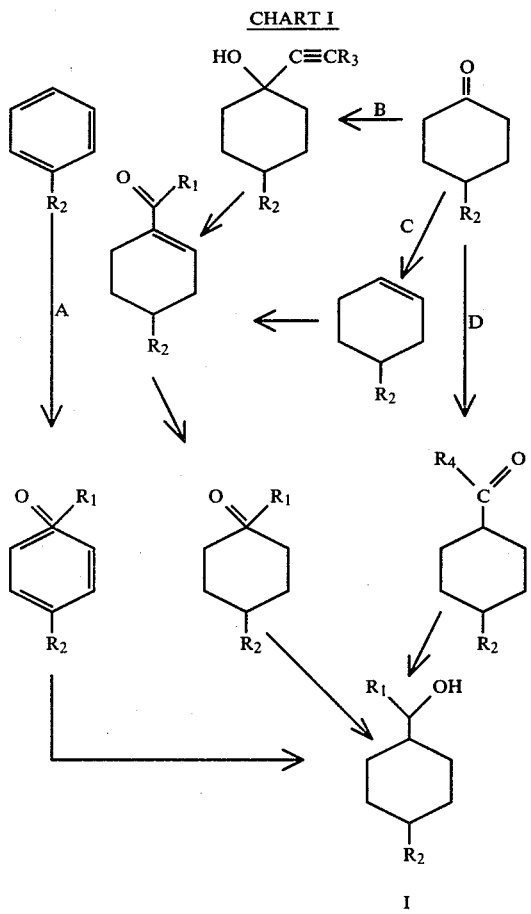

$R_1$ and $R_2$ are as previously defined
$R_3$ = H, $CH_3$, $C_2H_5$
$R_4$ = H, $CH_3$, $C_2H_5$, $C_3H_7$ In path A of Chart I, the t-alkylbenzene is alkanoylated via a Friedel Crafts type alkanoylation to provide a composition consisting essentially of the desired 4-t-alkylalkanoylbenzene. The ketone prepared is then hydrogenated in the presence of a suitable catalyst to provide the desired alcohol I.

In path B of Chart I, the 4-t-alkylcyclohexanone is reacted with the appropriate metal acetylide to provide the ethynyl alcohol which is converted to the appropriate alkanoylcyclohexene via the known Rupe rearrangement. The 4-t-alkyl-1-alkanoylcyclohexene is then reduced in either one or two steps to provide the desired alcohol I.

Path C illustrates a method by which the 4-t-alkylcyclohexanone is converted to the 4-t-alkylcyclohexene by reducing first to the alcohol and then dehydrating to provide the olefin. The olefin is then converted to a composition comprising the 4-t-alkyl-1-alkanoylcyclohexene via the known Kondakov reaction, the product then being converted to the desired alcohol I as previously indicated.

Path D illustrates another alternative which utilizes the well known Darzen's reaction to convert the 4-t-alkylcyclohexanone to the aldehyde ($R_4$=H) when esters of chloroacetic acid are used, or to ketones ($R_4 \neq H$) when esters of higher α-chloroacids are used. Ketones so produced can be converted to the desired alcohol I by an appropriate reduction of the carbonyl group. Aldehyde products of the Darzen's reaction can be converted to the desired alcohol I by reacting the aldehyde with an appropriate organometallic derivative such as an alkyl lithium reagent or Grignard reagent.

The compounds of the present invention fluid use as odorants and may be used in perfumes, soaps and other toilet goods. They are especially, though not exclusively, useful as replacements or partial replacements for natural sandalwood oil.

DESCRIPTION OF THE PREFERRED EMBODIMENTS

As indicated previously, the alcohols of this invention can be prepared in several ways. Some of the 1-alkanoyl-4-t-alkylbenzene, 1-alkanoyl-4-t-alkylcyclohexene and 4-t-alkylcyclohexylcarboxaldehyde (1-formyl-4-t-alkylcyclohexane) derivatives required as intermediates in this invention are known in the prior art or can be prepared by utilizing chemical reactions well known in the art such as those illustrated in Chart I. For example: 1-acetyl-4-t-butylcyclohexene has been reported by M. S. Newman et al., *J. Am. Chem. Soc.* 82, 4098 (1960); 1-formyl-4-t-butylcyclohexane has been reported by B. Cross et al., *J. Chem. Soc.*, 3895 (1960); and 4-t-butylacetophenone has been reported by J. C. Butler et al., *J. Am. Chem. Soc.*, 76, 1906 (1954).

In method A of Chart I it is preferred to reduce the 1-alkanoyl-4-t-alkylbenzene compounds to the desired alcohol I using either a rhodium or ruthenium catalyst in order to minimize hydrogenolysis.

Requirements regarding the amount of catalyst, solvent, reaction temperature, hydrogen pressure and reaction time (though probably not independent of one another) do not seem to be critical. It is preferred to use a 5% Rh/C or 5% Rh/alumina catalyst in amounts ranging from 0.5 to 10% by weight of the ketone charged. The hydrogenation is suitably carried out at temperatures between 25° C. and 60° C. and at pressures between 30 psi and 300 psi.

The use of a solvent is optional. The hydrogenation can be affected without a solvent or in a suitable inert solvent such as ethanol, acetic acid, pentane etc. The amounts of catalyst mentioned, the temperatures and pressures given as well as the solvents used are intented to illustrate, but not limit this invention.

Alternatively, the hydrogenation of this ketone can be accomplished in two steps by first reducing the carbonyl group to an alcohol by methods known in the art (e.g. $NaBH_4$, $LiAlH_4$, normal catalytic reduction etc.) followed by hydrogenation of the resulting benzylic alcohol using rhodium catalyst as previously described.

In accordance with methods B and C of Chart I, the 1-alkanoyl-4-t-alkylcyclohexene can be hydrogenated to the novel alcohol I by a number of methods known in the hydrogenation art for hydrogenating α,β-unsaturated ketones to saturated alcohols. A two-step process can be utilized in which one of the unsaturated moieties is reduced before the other. It is preferred, however, to reduce the 1-alkanoyl-4-t-alkylcyclohexene by hydrogenating both the olefin and the carbonyl in a single step process.

Requirements for the single step process regarding the amount of catalyst, solvent, reaction temperature, hydrogen pressure and reaction time (though probably not independent of one another) do not seem to be critical. A number of catalysts are known in the art to convert α, β-unsaturated ketones to saturated alcohols, e.g., Platinum, Palladium, Raney Nickel, Rhodium, Ruthenium.

We prefer to use the economical Raney Nickel since it was unexpectedly found that this catalyst produces a product in which the cis isomer predominates. Here again, conditions do not seem to be critical regarding temperature, solvent pressure, and amount of catalyst. (Separation of 1-(α-hydroxyethyl)-4-t-butylcyclohexane into its cis and trans isomers revealed that the desirable sandalwood odorant properties of this compound are due predominantly to the cis isomer).

The preferred amount of catalyst is between 5–15% of the amount of ketone charged. The preferred temperature range is between 80° C. and 120° C. and the preferred pressure range is from 60 psi to 600 psi. Solvents may be used but are not necessary as the hydrogenation proceeds in the absence of solvent. If solvents are used, the preferred ones are those having a low vapor pressure under the hydrogenation conditions. Such a list of temperature ranges, pressure ranges and catalyst amounts is given to illustrate preferred reaction conditions and is not intended to limit this invention. Conditions well outside the ranges given would be applicable in most cases. The fact that the product formed was enriched in the cis isomer when Raney Nickel was used as catalyst, was quite unexpected. A 1:1 mixture was expected as was found in the other methods tried.

In comparison, when Raney Nickel was used, the α-hydroxyalkyl-4-t-alkylcyclohexane produced was enriched in the cis isomer, the cis to trans isomer ratio being in the range of about 2-3 to 1.

In accordance with Method D, the 4-t-alkylcyclohexylcarboxaldehyde can be brought to reaction with the suitable metal alkyl $R_1M$ by utilizing a number of procedures known in the art. It is preferred to effect reaction by adding the aldehyde over a period of time to a solution of the metal alkyl in an appropriate reaction inert solvent and, upon completion of reaction, to decompose the initial adduct with a protonic source such as an acid.

The metal alkyl is suitably a Grignard reagent (e.g., $R_1MgX$ wherein X is Cl, Br or I) or lithium alkyl (e.g., $R_1Li$) all of which are commercially available or can be prepared by methods known in the art.

The solvent is preferably an ether such as ethyl ether, THF, etc., or an ether-hydrocarbon mixture such as ethyl ether-toluene, THF-toluene, THF-benzene etc. Such procedures are well known to those skilled in the art.

As mentioned, the compounds of this invention can be represented by the formula:

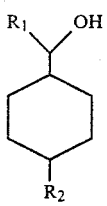

The essential features of $R_1$ and $R_2$ are that $R_1$ be a lower alkyl (not hydrogen) and that $R_2$ be a tertiary alkyl group wherein the tertiary alkyl carbon is attached to the cyclohexyl ring.

A finding of this invention is that compounds having the aforementioned structural features share in common an odoriferous note reminiscent of sandalwood. Compounds which do not have these essential features, i.e., if the alcohol is a primary or tertiary alcohol or the $R_2$ group is not tertiary alkyl, do not share the property of having a sandalwood odor.

Present data indicate that $R_1$ can be a lower alkyl from one to three carbon atoms and that $R_2$ can be a tertiary alkyl from four to eight carbon atoms. Initially it was believed that the lower molecular weight analog, the 1-(α-hydroxyethyl)-4-t-butylcyclohexane, had the more intense odor and was preferred. This view was reinforced as being consistent with the idea that the lower molecular weight compound would be more volatile and therefore probably more intense. Further testing has shown, surprisingly, that certain higher homologs are preferred. The final preference of one analog over another is most probably in the hands of the perfumer who will decide based on personal preference and/or the special requirements of the formulation he is creating.

Certain general tendencies do, however, seem to appear upon a comparison of the compounds. As one increases the bulk of the α-hydroxyethyl group from two to four carbons, the odor intensity seems to diminish with each carbon added. Therefore, it is especially preferred that $R_1$ be methyl as opposed to ethyl or propyl in those cases where odor intensity is important.

Changes in $R_2$ are less pronounced and seem unpredictable. While the simplest analog ($R_2$=t-butyl) has a fine intense sandalwood odor, a number of the higher homologs are preferred by some perfumers. Those analogs having $R_2$ as a five or six carbon moiety have fine intense sandalwood odors, perhaps stronger than the t-butyl analog. Those wherein $R_2$ is a seven carbon group seem less intense than the six carbon analogs, but still have fine sandalwood odors. Based on present observations, the sum of $R_2+R_1$ should not exceed ten carbon atoms. Thus, the preferred secondary alcohols of this invention would range between 12 and 17 carbon atoms, with 12 to 15 carbon atom alcohols having $R_1$ as methyl being especially preferred.

Separation of 1-(α-hydroxyethyl)-4-t-butylcyclohexane into its cis and trans isomers revealed that the desirable sandalwood odorant properties of that composition were due predominantly to the cis isomer. While this may create a presumption that the cis isomer of the higher homologs would be preferred, such data was not obtained since there is no commercially practical way to separate the isomers and since the mixture is a fine odorant in itself. (The pure cis-1-(α-hydroxyethyl)-4-t-butylcyclohexane appears to have little advantage, if any, over the mixture of isomers).

When blended with the aromatic oils, concentrates and chemicals used in the perfume arts, the novel α-hydroxyalkyl-4-t-alkylcyclohexanes of this invention impart natural sandalwood notes to such formulations. They are particularly useful for their use in formulations to replace or extend natural sandalwood oil.

For the most part, the aroma chemicals herein evaluated can be used in perfume formulations in a practical range extending from 0.1 to 30 percent. This will vary, of course, depending upon the type of fragrance formula involved. Concentrations above 30 percent, even as high as 80 or 90 percent, may be used successfully for special effects.

The compounds can be used to prepare odorant compositions which can be used as odorant bases for the preparation of perfumes and toilet waters by adding the usual alcoholic and aqueous diluents thereto: approximately 15–20% by weight of base would be used for the former and approximately 3–5% by weight would be used for the latter.

Similarly, the base compositions can be used to odorize soaps, detergents, cosmetics, or the like. In these instances, a base concentration of from about 0.5 to about 2% by weight can be used.

The following examples are provided to illustrate further the practice of the present invention, but are for purposes of preferred embodiments only and should not be construed as limiting.

Unless otherwise indicated, temperatures are in ° C., infrared bands are reported in inverse centimeters, nuclear magnetic resonance spectra were run in chloroform-$d_1$ and signals are reported in δ units relative to TMS (δ0.0), and molecular weights were determined by mass spectroscopy. Gas-liquid chromatography was also used to analyze the products.

EXAMPLE I

This example provides a general procedure to prepare the compounds of this invention according to path B of Chart I.

A. Preparation of t-alkylcyclohexanones

The procedure for preparing the 4-(3-methylpent-3-yl)cyclohexanone is offered for illustration. The other t-alkylcyclohexanones can be similarly prepared.

1. Preparation of 4-(3-methylpent-3-yl)cyclohexanone (a) Preparation of 4-(3-methylpent-3-yl)phenol A mixture of phenol (396 g, 4.2 mol), 3-methyl-3-pentanol (230 g. 2.25 mol), 85% phosphoric acid (50 g, 0.43 mol) and benzene (1.5 liters) was refluxed and the azeotroped water was collected in a Dean Stark trap (53 ml). The reaction mixture was cooled and transferred to a separatory funnel. A small bottom layer was separated and the top (organic) layer was washed with 500 ml portions of water until the pH of the washes was 7 (neutral). The solvent was removed on a rotary evaporator. Distillation of the residual oil under vacuum gave the desired 4-(3-methylpent-3-yl)phenol: 365 g, 91% yield; bp 112° C. (1.0 mm); mol wt. 178 (ms); nmr, 0.68 (6H, t, J=8 2-methyls), 1.26 (3H, s, methyl), 1.4–2.0 (4H, m, —CH$_2$—), 6.28 (1H, s, hydroxyl), 6.8–7.3 (4H, m, aromatics); ir, 3260, 2980, 2940, 2890, 1615, 1600, 1515, 1466, 1380, 1250, 1190, 1120, 830 cm$^{-1}$.

(b) Preparation of 4-(3-methylpent-3-yl)cyclohexanol

A mixture of the 4-(3-methylpent-3-yl)phenol (365 g, 2.05 mol), ethanol (600 g), acetic acid (5.0 g) and 5% rhodium on carbon (8.0 g) was hydrogenated at 100 psi and 60° C. until the hydrogen absorption essentially ceased. The reaction mixture was filtered to remove the catalyst and the solvent was removed on a rotary evaporator. The resulting oil was washed with 10% sodium bicarbonate (200 ml) and then with water (200 ml portions) until a neutral pH (7) was indicated. Distillation of the crude oil under vacuum gave the desired 4-(3-methylpent-3-yl)cyclohexanol: 350 g, 93% yield; bp 110°–115° C. (2.0 mm); mol wt 184 (ms); nmr, 0.4–0.9 (9H, methyls), 1.0–1.5 (14H, m, CH$_2$), 2.39 (1H, s, hydroxyl), 4.0 (1H, m, H$\alpha$ to oxygen); ir, 3350, 2980, 2950, 2890, 1455, 1385, 1075, 1046, 960 cm$^{-1}$.

(c) Preparation of 4-(3-methylpent-3-yl)cyclohexanone

The 4-(3-methylpent-3-yl)cyclohexanol (350 g, 1.9 mol) prepared above was added slowly over a 3 hour period to a stirring solution of sodium dichromate (614 g, 2.06 mol), water (3.0 liters) and 98% sulfuric acid (526 g) while maintaining the batch temperature at 50°–55° C. Upon completion of the addition, the mixture was stirred an additional hour at 50° C. The reaction mixture was cooled and three liters of benzene was added. The layers were separated and the organic layer washed with one liter portions of water until a neutral pH was indicated. The solvent was removed on a rotary evaporator. Distillation of the residual oil under vacuum gave the desired 4-(3-methylpent-3-yl)cyclohexanone: 274 g, 79% theory; bp 105° C. (0.5 mm); mol wt 182 (ms); nmr, 0.75 (3H, s, methyl, 0.8 (6H, t, J=7, methyls), 1.15–2.0 (9H, m, CH, CH$_2$), 2.15–2.5 (4H, m, H$\alpha$ to carbonyl); ir, 2980, 2890, 1720, 1465, 1390, 1170 cm$^{-1}$.

2. In a like manner, other t-alkylcyclohexanones of this invention can be prepared by utilizing the appropriate tertiary alcohol in the above procedure. Among those prepared were:
(a) 4-(2-methylpent-2yl)cyclohexanone bp 88°–90° C. (1.0 mm)
(b) 4-(3-ethylpent-3-yl)cyclohexanone bp 79°–80° C. (0.3 mm)
(c) 4-(1-methylcyclopentyl)cyclohexanone bp 110° C. (0.5 mm)
(d) 4-(1-methylcyclohexyl)cyclohexanone mp 47°–8° C. (solid)

All of the above compounds had ir, nmr and ms spectra consistent with their structure.

B. Preparation of 1-acetyl-4-t-alkylcyclohexenes

The procedure for preparing 1-acetyl-4-t-amylcyclohexene is offered for illustration. The other 1-acetyl-4-t-alkylcyclohexenes can be prepared similarly.

1. Acetyl-4-t-amylcyclohexene

To a stirred mixture of 46 g of lithium acetylide in 200 ml of benzene was added, 84.0 g (0.5 mol) of 4-t-amylcyclohexanone over a period of 3 hr. The mixture was stirred for an additional hour. Water (500 ml) was then added dropwise and the mixture was refluxed for 1 hr. The mixture was allowed to cool and was separated. The aqueous phase was extracted with ether. The combined organic phase was washed with water, dried over magnesium sulfate, filtered, and concentrated under reduced pressure. Distillation of the residual oil gave cis and trans-4-t-amyl-1-ethynylcyclohexanol: 49.8 g, 51% yield, bp 103°–104° (0.5–1.0 mm); nmr, 2.48 (1H, s, ethynyl H), 0.78 (9H, methyl H); ir, 3380, 3300, 1064 cm$^{-1}$.

A solution of 24.0 g (0.12 mol) of cis and trans-4-t-amyl-1-ethynylcyclohexanol and 75 ml of 90% formic acid was heated under reflux for 2 hr. The solution was allowed to cool. Excess 10% sodium hydroxide solution was added dropwise and the mixture extracted with ether. The etherial extract was washed with water, dried over magnesium sulfate, filtered, and concentrated under reduced pressure. Distillation of the residual oil gave 1-acetyl-4-t-amylcyclohexene: 13.2 g, 55% yield; bp 63°–64° (0.1 mm); mol wt 194 (ms); nmr, 6.93 (1H, broad, vinylic H), 2.25 (3H, s, acetyl methyl), 0.82 (9H, methyl H); ir, 1662, 1639, 1385, 1248, 1068, 964, 907 cm$^{-1}$.

2. In a like manner, other 1-acetyl-4-t-alkylcyclohexenes of this invention can be prepared by utilizing the appropriate ketone in the above procedure. Among those prepared were:
(a) 1-Acetyl-4-(3-methylpent-3-yl)cyclohexene bp 84°–6° C.(0.15 mm)
(b) 1-Acetyl-4-(2-methylpent-2-yl)cyclohexene bp 82°–4° C.(0.15 mm)
(c) 1-Acetyl-4-(3-ethylpent-3-yl)cyclohexene bp 95°–100° C.(1.0 mm)
(d) 1-Acetyl-4-(1-methylcyclopentyl)cyclohexene bp 88°–90° C. (0.3 mm)
(e) 1-Acetyl-4-(1-methylcyclohexyl)cyclohexene bp 92°–100° C. (0.15 mm)

All the above compounds had ir, nmr and ms spectra consistent with their structure.

C. Preparation of 1-($\alpha$-hydroxyethyl)-4-t-alkylcyclohexanes from the 1-acetyl-4-t-alkylcyclohexenes.

The procedure for preparing the 1-($\alpha$-hydroxyethyl)-4-t-butylcyclohexane is offered for illustration. The other 1($\alpha$-hydroxyethyl)-4-t-alkylcyclohexenes can be similarly prepared.

1. 1-($\alpha$-Hydroxyethyl)-4-t-Butylcyclohexane from 1-acetyl-4-t-butylcyclohexene (a) Two Step Process A solution of 70 g (0.39 mol) of 1-acetyl-4-t-butylcyclohexene in 200 ml ethanol was hydrogenated with 0.5 g of 5% palladium on charcoal on a Parr hydrogenation apparatus under 50 psi hydrogen pressure. When the theoretical amount (0.39 mol) of hydrogen was absorbed, the reaction was stopped, the mixture filtered, concentrated, and distilled under reduced pressure to give ca. 1:1 mixture of cis and trans-1-acetyl-4-t-butylcyclohexane: 64.6 g, 91% yield; bp 64°–92° C. (8 mm); mol wt. 182 (ms); nmr shows no vinylic hydrogen.

A solution of 30 g (0.16 mol) of this 1:1 mixture of cis and trans-1-acetyl-4-t-butylcyclohexane in 30 ml anhydrous ether was added dropwise to a stirred mixture of 4 g lithium aluminum hydride in 200 ml anhydrous ether. After addition, the mixture was heated under reflux for 5 hours, allowed to cool, and saturated ammonium chloride solution was added dropwise until a clear ether layer was obtained. The mixture was filtered, washed with 10% sodium hydroxide solution, washed with water, dried, concentrated, and distilled to give a 1:1 mixture of cis and trans-1-($\alpha$-hydroxyethyl)-4-t-butylcyclohexane: 25.0 g, 83.3% yield; bp 75°–85° C. (2 mm); mol wt 184; nmr, no absorption between 2.0–2.2 (acetyl methyl H); ir 3330 (hydroxyl).

(b) Single Step Process with Raney Nickel in Solvent

A mixture of 353 g (2.0 mol) of 1-acethyl-4-t-butylcyclohexene, 100 ml of n-butanol, and 35 g of Raney Nickel (activated by repeated washing with methanol) was hydrogenated at 100° with 300 psi hydrogen pressure until hydrogen uptake essentially stopped (3.1 moles hydrogen consumed, 78% of the theoretical amount). The catalyst was removed by filtration, replaced with fresh catalyst, and the reaction resumed until the remaining 0.9 mole of hydrogen was consumed. After filtration and removal of solvent, the crude product 1-($\alpha$-hydroxyethyl)-4-t-butylcyclohexane consisted of 77% of the cis isomer and 23% of the trans isomer.

(c) Single Step Process with Raney Nickel without Solvent

A mixture of 200 g (1.11 mol) of 1-acetyl-4-t-butylcyclohexene and 20 g of Raney Nickel (activated by repeated washing with methanol) was hydrogenated at 100° with 300 psi hydrogen pressure until hydrogen uptake ceased (2.2 moles hydrogen consumed). After filtration, the crude product 1-($\alpha$-hydroxyethyl)-4-t-butylcyclohexane consisted of 64% of the cis isomer and 36% of the trans isomer, uncontaminated with any 1-acetyl-4-t-butylcyclohexane.

2. In a like manner, other 1-($\alpha$-hydroxyethyl)-4-t-alkylcyclohexanes of this invention can be prepared by utilizing the proper 1-acetyl-4-t-alkylcyclohexene in the above procedures. Among those prepared were:

(a) 1-($\alpha$-Hydroxyethyl)-4-(2-methylbut-2-yl)cyclohexane, also known as 1-($\alpha$-hydroxyethyl)-4-t-amylcyclohexane; bp 89–94 (1 mm); mol wt 198 (ms); nmr, 1.20 (0.5H, d, J=6 Hz, methyl $\alpha$ to OH in cis isomer), 1.15 (0.5H, d, J=6 Hz, methyl $\alpha$ to OH in trans isomer), 0.77 (9H, sharp, methyl H); ir, 3360, 1455, 1070, 935 cm$^{-1}$.

(b) 1-($\alpha$-Hydroxyethyl)-4-(2-methylpent-2-yl)cyclohexane; bp 95–100 (1 mm); mol wt 212 (ms); nmr 0.75 (s, methyls) 0.8–1.9 (m, —CH$_2$, CH, methyl $\alpha$ to oxygen), 2.08 (1H, s, hydroxyl), 3.43 (m, H$\alpha$ to oxygen cis-isomer), 3.86 (m, H$\alpha$ to oxygen trans-isomer); ir, 3380, 2980, 2940, 2880, 1475, 1455, 1390, 1370, 1070, 940 cm$^{-1}$.

(c) 1-($\alpha$-Hydroxyethyl)-4-(3-methylpent-3-yl)cyclohexane; bp 82–83 (0.15 mm); mol wt 212 (ms); nmr 0.66 (3H, s, methyl) 0.71 (6H, t, J=7, methyls), 1.05–1.85 (14H, m, CH$_2$, CH), 1.96 (1H, s, hydroxyl), 3.46 (q, J=7, H$\alpha$ to oxygen in cis isomer) 3.88 (m, H$\alpha$ to oxygen, trans-isomer); ir, 3360, 2980, 2940, 2890, 2880, 1460, 1385, 940 cm$^{-1}$.

(d) 1-($\alpha$-Hydroxyethyl)-4-(3-ethylpent-3-yl)cyclohexane; bp 120–130 (0.5 mm); mol wt 226 (ms); nmr, 0.7–0.95 (m, methyls), 1.0–1.9 (m, CH$_2$, CH, methyl $\alpha$ to hydroxyl), 1.9 (1H, s, hydroxyl), 3.5 (m, H$\alpha$ to hydroxy cis-isomer), 3.9 (m, H$\alpha$ to hydroxyl trans-isomer); ir, 3350, 2980, 2940, 2890, 1655, 1380, 1075, 940 cm$^{-1}$.

(e) 1-($\alpha$-Hydroxyethyl)-4-(1-methylcyclopentyl)cyclohexane; bp 114–120 (0.5 mm); mol wt 210 (ms); nmr, 0.81 (3H, s, methyl on cyclopentyl), 1.0–1.8 (m, CH$_2$, CH, methyl $\alpha$ to hydroxyl), 1.71 (1H, s, hydroxyl), 3.5 (m, H$\alpha$ to hydroxyl cis-isomer), 3.9 (m, H$\alpha$ to hydroxyl trans-isomer); ir, 3360, 2950, 2870, 1455, 1380, 1070, 940 cm$^{-1}$.

(f) 1-($\alpha$-Hydroxyethyl)-4-(1-methylcyclohexyl)cyclohexane; bp 130–140 (1.0 mm), mol wt 224 (ms), nmr, 0.73 (3H, s, methyl) 0.9–1.8 (23H, m CH$_2$ CH, methyl $\alpha$ to hydroxyl), 1.75 (1H, s, hydroxyl), 3.51 (m, H$\alpha$ to hydroxyl, cis-isomer), 3.91 (m, H$\alpha$ to hydroxyl, trans-isomer); ir, 3380, 2940, 2870, 1455, 1380, 1070, 940 cm$^{-1}$.

EXAMPLE II

Preparation of pure cis-1-($\alpha$-Hydroxyethyl)-4-t-butylcyclohexane and pure trans-1-($\alpha$-hydroxyethyl)-4-t-butylcyclohexane.

The followig example illustrates how the pure isomers can be prepared.

A mixture of cis and trans 1-acetyl-4-t-butylcyclohexane as prepared in Example ICla was separated into its pure components by vacuum distillation on a Nester-Faust spinning band distillation apparatus. The physical constants of the two isomers are as follows:

cis-1-Acetyl-4-t-butylcyclohexane: mol wt 182 (ms); bp 84°–86° C. (8 mm); 0.80 (9H, s, t-butyl H), 2.12 (3H, s, acetyl methyl H); ir, 1710, 1365, 1355, 1175, 1140.

trans-1-Acetyl-4-t-butylcyclohexane: mol wt 182 (ms); bp 92°–93° C. (8 mm); nmr, 0.85 (9H, s, t-butyl H), 2.10 (3H, s, acetyl methyl H); ir, 1710, 1365, 1250, 1168.

The cis isomer was epimerized in a refluxing solution of sodium carbonate in aqueous methanol to a 90%:10% mixture of trans:cis-1-acetyl-4-t-butylcyclohexane. The spectral data of this mixture was essentially identical with that obtained for the pure trans isomer.

Each of the pure 1-acetyl-4-t-butylcyclohexane isomers were converted to their respective alcohols with lithium aluminum hydride as described in Example ICla. The physical constants of the two isomers are as follows:

cis-1-($\alpha$-Hydroxyethyl)-4-t-butylcyclohexane: mol wt 184 (ms); bp 75°–77° C. (2 mm); nmr, 0.85 (9H, s, t-butyl H), 1.0–1.8 (13 H, m, methyl d at 1.22, J=6 Hz), 3.93 (1H, m, H$\alpha$ to OH); ir, 3330, 1365, 1240, 1235, 1065, 935, 880.

trans-1-($\alpha$-Hydroxyethyl)-4-t-butylcyclohexane: mol wt 184 (ms); bp 80–85 (2 mm); nmr, 0.85 (9H, s, t-butyl H), 1.0–1.8 (13 H, m, with methyl d at 1.16, J=6.5 Hz), 3.53 (1H, m, H$\alpha$ to OH); ir, 3340, 1365, 1235, 1150, 1068, 950, 940, 930, 900, 880.

The desirable sandalwood odorant properties of 1-($\alpha$-hydroxyethyl)-4-t-butylcyclohexane are due predominantly to the cis isomer.

The foregoing result may create a presumption that the cis isomer of other analogs described herein would be preferred over the corresponding trans isomers. Such data was not obtained, however, since no commercially feasible way of separating the isomers was known and since the mixture has a fine odor in itself.

EXAMPLE III

Preparation of 1-($\alpha$-hydroxyalkyl)-4-t-alkylcyclohexanes from 1-alkanoyl-4-t-alkylbenzenes.

The procedure for preparing 1-($\alpha$-hydroxyethyl)-4-t-butylcyclohexane from 4-t-butylacetophenone is offered for illustration. Other 1-($\alpha$-hydroxyalkyl)-4-t-alkylcyclohexanes can be similarly prepared from the appropriate 4-t-alkylacetophenones.

(1) cis and trans-1-(α-Hydroxyethyl)-4-t-butylcyclohexane from 4-t-Butylacetophenone A mixture of 17.6 g (0.10 mol) of 4-t-butyl-acetophenone, 1.3 g of 5% rhodium on alumina, a few drops of acetic acid, and 10 ml of absolute ethanol was hydrogenated on a Parr apparatus under a hydrogen pressure of 50 psi at ambient temperature until hydrogen uptake ceased. By glc, the hydrogenate contained 8% of 1-acetyl-4-t-butylcyclohexane. The catalyst was then removed by filtration and the above procedure repeated until hydrogen uptake again ceased. The mixture was filtered, concentrated under reduced pressure, and distilled to give 16.8 g (91% yield) of a 1:1 mixture of cis- and trans-1-(α-hydroxyethyl)-4-t-butylcyclohexane. The spectral properties were the same as described in Example I.

The same result was obtained when the solvent was acetic acid, ethanol, or pentane, or when the catalyst was 5% rhodium on charcoal, or when the temperature was 60°, or when the pressure was 300 psi.

The same result was obtained when 1-(α-hydroxyethyl)-4-t-butylbenzene was hydrogenated instead of 4-t-butylacetophenone.

Rather than repeat the hydrogenation to remove the small amount of 1-acetyl-4-t-butylcyclohexane present in the initial hydrogenate, this impurity can be removed from the 1-(α-hydroxyethyl)-4-t-butylcyclohexane by vacuum distillation.

EXAMPLE IV

This example provides a general procedure for preparing the compounds of this invention according to path D of Chart I.

The procedure for preparing 1-(α-hydroxypropyl)-4-t-butylcyclohexane is offered for illustration. The other analogs can be similarly prepared.

(1) 1-(1-Hydroxypropyl)-4-t-butylcyclohexane

To a mixture of 24 g (1.0 mol) magnesium turnings and 100 ml anhydrous ethyl ether was added 109 g (1.0 mol) bromoethane. The resulting solution was heated under reflux for two hours. To the above solution, 109 g (0.9 mol) 1-formyl-4-t-butylcyclohexane was added dropwise over 1 hour. After addition, the mixture was heated under reflux for four hours, allowed to cool, and then added to 100 ml of a mixture of saturated ammonium chloride solution and ice. The mixture was extracted with ether (3×100 ml) and the extract washed with water, dried, concentrated, and distilled to give a 1:1 mixture of cis and trans-1-(1-hydroxypropyl)-4-t-butylcyclohexane: 116 g (66% yield); bp 89–95 (1 mm); mol wt 198 (ms); nmr 0.85 (12 H, s, methyl H), 3.1–3.9 (1H, broad, αH); ir, 3350, 1364, 970.

(2) 1-(α-Hydroxy-2-methylprop-1-yl)-4-t-butylcyclohexane

This compound was similarly prepared using 2-bromopropane. Distillation of the product yielded a 1:1 mixture of cis and trans-1-(1-hydroxy-2-methylprop-1-yl)-4-t-butylcyclohexane; 77 g, 73% yield; bp 98–110 (3 mm); mol wt 212 (ms); nmr, 0.82 (15 H,s, t-butyl and isopropyl methyl H), 3.0–3.8 (1H, broad, αH); ir, 3360, 1360, 1110, 1000, 980.

EXAMPLE V

This example, along with the following examples, is offered to illustrate the utility of this invention in fragrance compositions.

The compounds of this invention are particularly useful in the creation of synthetic sandalwood oil substitutes or sandalwood specialties. In the following formulation, X represents a compound of this invention or the odorless diethyl phthalate. The diethyl phthalate is used to illustrate the formulation without the novel compound.

| | |
|---|---|
| X | 200 |
| *Sandela ®, 50% in Diethyl phthalate | 700 |
| Amyris Oil | 50 |
| American Cedarwood Oil | 50 |
| | 1,000 |

*Registered Trademark of Givaudan Corporation for a polycyclic alcohol product having a sandalwood odor.

X can represent any of the novel compounds of this invention, each of which makes a contribution to the composition. By comparing the compositions containing one of the novel compounds with the composition wherein X is the odorless diethyl phthalate, the contribution is quite evident.

While each of the novel compounds offer subtle differences of degree in their contribution, the odor of the composition without the novel compound is weaker and less reminiscent of the natural sandalwood oil.

As expected from their individual odor strengths, the contribution of the compounds where $R_1$ is methyl is stronger than those where $R_1$ is a higher analog.

Especially preferred in this formulation were those compounds having the more intense odors, i.e., 1-(α-hydroxyethyl)-4-t-butylcyclohexane, 1-(α-hydroxyethyl)-4-(2-methylpent-2-yl)cyclohexane, 1-(α-hydroxyethyl)-4-(3-methylpent-3-yl)cyclohexane, or 1-(α-hydroxyethyl)-4-(1-methylcyclopentyl)cyclohexane.

With other analogs, e.g., 1-(α-hydroxyethyl)-4-(1-methylcyclohexyl)cyclohexane, 1-(α-hydroxyethyl)-4-(3-ethylpent-3-yl)cyclohexane etc., it may be preferred to use higher levels in the formulation, perhaps 30 to 40%.

The above formulation and discussions with respect to it are provided purely for illustration. It is expected that in each case the compound (or mixtures of them) chosen as X would be subject to the individual perfumers perferences and needs. The experienced perfumer would be expected to use his expertise to take advantage of the subtle nuances by which each of the compounds differ in compounding a new formulation.

Depending on the perfumer's needs, compounds of this invention can be used in a range of concentration from 10–60% by weight.

EXAMPLE VI

The following example is offered to illustrate the utility of the sandalwood compositions of this invention in fragrance compositions of the woody type. Once again, in the formulation below, X is used to represent a novel compound of this invention or an equivalent amount of the odorless diethyl phthalate.

| Component | Pts |
|---|---|
| X | 280 |

| Component | Pts |
| --- | --- |
| Oranger liquid | 20 |
| Limonene | 38 |
| Linalool | 66 |
| Linalyl acetate | 95 |
| Benzyl acetate | 20 |
| γ-Methyl ionone | 152 |
| p-tert.-Butylcyclohexyl acetate | 114 |
| Vetiver acetate | 115 |
| Coumarin | 40 |
| Versalide ®* | 30 |
| Aldehyde C-12, 10% DPG | 4 |
| Undecalactone, 10% DPG | 6 |
| Diphenyl oxide | 10 |
| Diphenyl methane | 10 |
| Total | 1,000 |

*Registered Trademark of Givaudan Corporation for 1,1,4,4-tetramethyl-6-ethyl-7-acetyl-1,2,3,4-tetrahydronapthalene.

Compositions containing 1-(α-hydroxyethyl)-4-t-butylcyclohexane, 1-(α-hydroxyethyl)-4-t-amylcyclohexane, and 1-(α-hydroxyethyl)-4-(3-methylpent-3-yl)cyclohexane were compared with the formula wherein X was diethyl phthalate. In each case, the novel compound of this invention made the odor richer and smoother, and had an effect similar to that achieved by adding natural sandalwood oil.

Other compounds of this invention can be used with similar results. Higher concentrations can be used in such a formulation for unique and special effects.

EXAMPLE VII

The following example is offered to illustrate the utility of the sandalwood compounds of this invention in fragrance compositions of the woody-floral type. As before, X represents either the compound added or the odorless diethyl phthalate.

| Component | Pts |
| --- | --- |
| X | 300 |
| Amyl cinnamic aldehyde | 21 |
| Aldehyde C-12 (Lauric) in 10% Dipropylene glycol | 8 |
| Benzyl propionate | 25 |
| Bergamot natural | 22 |
| Methyl phenyl carbinyl acetate | 14 |
| Linalool, coeur | 35 |
| Ylang bourbon extra | 14 |
| γ-Methyl ionone | 100 |
| Jasmin synthetic | 35 |
| α-Methyl-β-(p-tert-butylphenyl)propionaldehyde | 70 |
| p-tert-Butylcyclohexyl acetate | 97 |
| Vetiver acetate | 97 |
| 3,7-Dimethyl-7-octenol | 56 |
| 1,1,4,4-Tetramethyl-6-ethyl-7-acetyl-1,2,3,4-tetrahydronaphthalene | 56 |
| Undecalactone, 10% in Dipropylene glycol | 8 |

The formulation with X as 1-(α-hydroxyethyl)-4-(1-methylcyclopent-1-yl)-cyclohexane was compared with the one that had X as diethyl phthalate. The odor of the fragrance having the novel compound was richer and smoother than the fragrance without it. The effect achieved by the addition of the novel compound was similar to the effect achieved by the addition of natural sandalwood oil.

In a similar fashion, other compounds of this invention can be used as X with similar effects.

EXAMPLE XIII

The following example illustrates the utility of the novel compounds of this invention in fragrance compositions of the muguet type. The term X represents a novel compound of this invention or the odorless diethyl phthalate.

| Component | Pts |
| --- | --- |
| X | 142 |
| Aldehyde C-9, n-nonanal, 10% diethyl phthalate | 2.3 |
| Aldehyde C-10, n-decanal, 10% DEP | 1 |
| Amyl cinnamic aldehyde | 13 |
| Benzyl acetate | 25 |
| Benzyl salicylate | 20 |
| Cinnamyl acetate | 45 |
| Cyclamen aldehyde, α-methyl-p-isopropylphenylpropionaldehyde | 10 |
| Citronellyl acetate | 30 |
| Phenyl methyl carbinyl acetate, 10% DEP | 45 |
| Hexyl cinnamic aldehyde | 20 |
| Indole, 2,3-benzylpyrrole, 10% DEP | 4 |
| Laurine ®, Hydroxycitronellal | 120 |
| Linalool, coeur | 140 |
| Linalyl cinnamate | 40 |
| Nerol, prime | 40 |
| Phenyl ethyl alcohol | 130 |
| Phenyl ethyl isobutyrate | 4 |
| Phenyl ethyl dimethyl carbinol | 10 |
| Phenyl ethyl phenyl acetate | 25 |
| Rhodinol, extra | 60 |
| Rhodinyl acetate | 34 |
| Terpineol | 50 |
| Tetrahydrolinalool | 30 |
| | 1,000 |

The addition of 1-(α-hydroxyethyl)-4-(1-methylcyclopent-1-yl)cyclohexane as X above imparts a naturalness to the composition by imparting woody and stem notes thus making the odor more of the whole flower in its natural environment. The effect is reminiscent of the contribution made by natural sandalwood oil. The composition with diethyl phthalate as X lacks such qualities.

Other novel compounds of this invention can be used as X with similar effects.

What is claimed is:

1. A compound of the formula

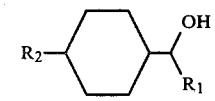

wherein:
R₁ is selected from the group consisting of from one to three carbon atoms;
R₂ is selected from the group of tertiary alkyl radicals of four to eight carbon atoms;
The carbon of R₂ bonded to the cyclohexyl ring is the tertiary carbon;
The number of carbon atoms in R₁+R₂ does not exceed ten.

2. A compound according to claim 1 wherein R₁ is methyl.

3. A compound according to claim 2 wherein R₂ has from four to seven carbon atoms.

4. 1-(α-Hydroxyethyl)-4-(1-methylcyclohex-1-yl)cyclohexane.

5. 1-(α-Hydroxyethyl)-4-(3-ethylpent-3-yl)cyclohexane.

6. A compound according to claim 2 wherein $R_2$ has from four to six carbon atoms.

7. 1-($\alpha$-Hydroxyethyl)-4-(2-methylpent-2-yl)cyclohexane.

8. 1-($\alpha$-Hydroxyethyl)-4-(3-methylpent-3-yl)cyclohexane.

9. 1-($\alpha$-Hydroxyethyl)-4-(1-methylcyclopent-1-yl)cyclohexane.

10. 1-($\alpha$-Hydroxyethyl)-4-t-amylcyclohexane 11. 1-($\alpha$-Hydroxyethyl)-4-t-butylcyclohexane.

12. cis-1-($\alpha$-Hydroxyethyl)-4-t-butylcyclohexane.

13. A method for improving the odor of fragrance compositions which comprises adding thereto the compound of claim 3 in an amount sufficient to impart a sandalwood odor.

14. A method for improving the odor of fragrance compositions which comprises adding thereto the compound of claim 6 in an amount sufficient to impart a sandalwood odor.

15. A method according to claim 14 wherein the compound added is 1-($\alpha$-hydroxyethyl)-4-t-butylcyclohexane.

16. A method according to claim 14 wherein the compound added is 1-($\alpha$-hydroxyethyl)-4-t-amylcyclohexane.

17. A method according to claim 14 wherein the compound added is 1-($\alpha$-hydroxyethyl)-4-(1-methylcyclopent-1-yl)cyclohexane.

18. A method according to claim 14 wherein the compound added is 1-($\alpha$-hydroxyethyl)-4-(3-methylpent-3-yl)cyclohexane.

19. A method according to claim 14 wherein the compound added is 1-($\alpha$-hydroxyethyl)-4-(2-methylpent-2-yl).

20. A fragrance composition comprising an olfactorily effective amount of a compound of claim 3 and at least one other olfactory ingredient.

21. A fragrance composition comprising an olfactory effective amount of a compound of claim 6 and at least one other olfactory ingredient.

22. A fragrance composition according to claim 21 comprising an olfactorily effective amount of 1-($\alpha$-hydroxyethyl)-4-t-butylcyclohexane.

23. A fragrance composition according to claim 21 comprising an olfactorily effective amount of 1-($\alpha$-hydroxyethyl)-4-t-amylcyclohexane.

24. A fragrance composition according to claim 21 comprising an olfactorily effective amount of 1-($\alpha$-hydroxyethyl)-4-(1-methylcyclopent-1-yl)cyclohexane.

25. A fragrance composition according to claim 21 comprising an olfactorily effective amount of 1-($\alpha$-hydroxyethyl)-4-(3-methylpent-3-yl)cyclohexane.

26. A fragrance composition according to claim 21 comprising an olfactorily effective amount of 1-($\alpha$-hydroxyethyl)-4-(2-methylpent-2-yl)cyclohexane.

* * * * *